Figure 1:
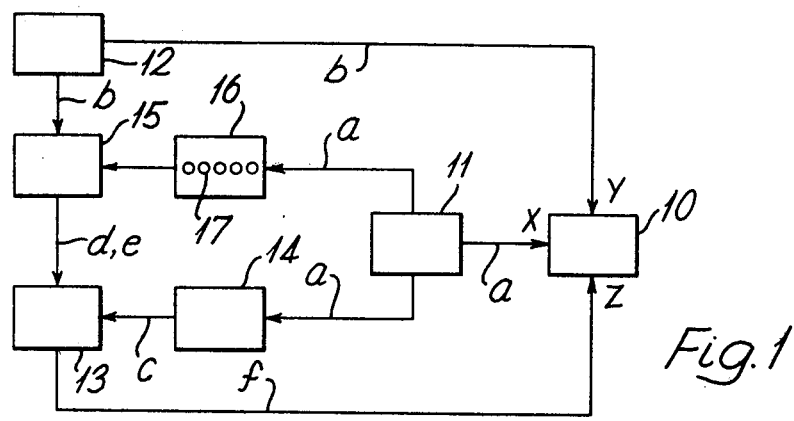

United States Patent [19]

Dobson et al.

[11] 4,293,200

[45] Oct. 6, 1981

[54] VISUAL FACULTY TESTING APPARATUS

[76] Inventors: John S. Dobson, 6 Broadacres, Cathorpe Park, Fleet, Hampshire, England; Peter A. Davison, Sea View, Seapoint Rd., Bray, County Wicklow, Ireland

[21] Appl. No.: 128,816

[22] Filed: Mar. 10, 1980

[30] Foreign Application Priority Data

Mar. 12, 1979 [GB] United Kingdom ............... 08598/79

[51] Int. Cl.³ .............................................. A61B 3/02
[52] U.S. Cl. ......................................... 351/36; 351/32
[58] Field of Search ...................... 351/36, 32, 33, 30, 351/37

[56] References Cited

PUBLICATIONS

Engel, Simulating Accommodation by Image Autocorrelations, American Journal of Optometry and Archives of American Academy of Optometry, Jun. 1972.

Primary Examiner—John K. Corbin
Assistant Examiner—Rodney B. Bovernick
Attorney, Agent, or Firm—Cushman, Darby & Cushman

[57] ABSTRACT

Visual faculty testing apparatus is proposed to facilitate contrast sensitivity assessment. Existing procedures are limited and involve the presentation to a subject of a target of which the overall contrast is varied to determine the minimum level at which it is detectable. The present apparatus differs by presenting a target array of light and dark areas alternating in one direction, and with the luminance of at least one set of areas varying towards that of the other set in another direction, the apparatus including control means affording adjustment of the rate of this luminance variation whereby points of minimum contrast detection can be moved across the target. The amount of adjustment for each movement to prescribed subjectively judged positions or target patterns then gives a comparative basis for contrast sensitivity. The existing procedures commonly involve successive presentation of grating targets of respectively different uniform spacial frequency, with the minimum contrast detection levels being plotted against frequency in a contrast sensitivity function characteristic, and is time-consuming. The procedure can be compacted by use of the present apparatus in a preferred form to present a single target with progressively varying spacial frequency in the one direction, and by the provision of a plurality of controls for luminance variation rate adjustment in respective zones across the target in said one direction.

8 Claims, 4 Drawing Figures

U.S. Patent    Oct. 6, 1981    Sheet 1 of 2    4,293,200

VISUAL FACULTY TESTING APPARATUS

The present invention concerns visual faculty testing and is applicable to the testing of various visual functions. However, the invention has been developed initially with the intention of application to the testing of contrast sensitivity and it is appropriate to describe the invention with more particular reference to this application.

There is in fact an effective absence of contrast sensitivity function determination in routine clinical and other practice notwithstanding the obvious relevance of this function to many situations in everyday life, such as driving a motor vehicle. Moreover, there appears to be a correlation between some pathological conditions of the visual faculty and characteristics representing contrast sensitivity function.

This absence of contrast sensitivity function determination is due to the absence of a procedure suitable for routine usage. The existing procedures are limited and commonly follow the work of Campbell and co-workers (Campbell, F. W. and Green, D. G. 1965, J. Physiol. 181, 576) involving the successive presentation to a subject of targets in the form of gratings of respectively differing uniform spacial frequencies, the subject being able to alter the degree of contrast with which each grating is presented and thereby determine the minimum contrast levels at which he can detect the gratings. These levels can then be plotted against grating frequency to provide a contrast sensitivity function characteristic for the subject, but the overall procedure is clearly very time-consuming and is accordingly unsuited to use other than in special circumstances, such as academic study.

An object of the present invention is to obviate this situation and to this end there is provided, in accordance with a particular form of the invention, visual faculty testing apparatus comprising: means for presenting a visual target to a subject under test, said target being of overall luminance of a predetermined level, said target including an array of two sets of areas of respectively different luminance, said areas of said two sets being in an alternating sequence of progressively varying dimensions in one co-ordinate direction across said array, and said areas of said two sets being of progressively varying luminance in respectively equal and opposite manner towards said predetermined level in another co-ordinate direction across said array; and a plurality of control means respectively operably associated with different zones of said target successively located across said array in said one direction, said control means being selectively adjustable by said subject to alter the respective rates of luminance variation for said zones along said other direction.

It will be appreciated that adjacent areas of the target array are of respectively different luminance in said other direction up to the point where they each have a luminance equal to the predetermined level, but in practice such areas will be visually indistinguishable by a subject under test before this point is reached, the minimum detectable luminance difference depending upon the subject's contrast sensitivity. Moreover it will be appeciated that this minimum detectable luminance difference varies with the spacial frequency of the adjacent areas in question, and that this frequency progressively varies across the array in said one direction.

Given this appreciation, it remains to note that adjustment of the control means serves to move the points of luminance equality, both the absolute and the subjectively-judged therewith, and that the control means are respectively associated with zones of different spacial frequency, and it will be understood that a subject can be asked to adjust the subjectively-judged equal luminance points to form the target array to a pre-determined pattern whereat the degree of adjustments necessary relative to prescribed levels represent a contrast senstivity function characteristic for the subject.

The benefit of this procedure relative to the prior ones mentioned above lies in the fact that the spacial frequency dependence of contrast sensitivity is taken into account with the use of a single target.

The target array is conveniently in the general form of a rectangular grating composed of parallel bars, with the luminance variation extending along the bars and the spacial frequency variation extending across the bars. In this situation, a suitable predetermined pattern for attainment by a subject involves adjustment of the limiting points of distinctiveness of the bars to lie on a straight line thereacross.

However, it is possible to employ other forms of array such as generally star shaped or other polar co-ordinate forms, and also other forms of predetermined patterns such as involving limiting points on a circle or other curve.

It is also preferred that adjacent bars of respectively different luminance in the transverse direction across the grating should be smoothly merged, with the luminance in such direction suitably varying sinusoidally about a mean level equal to said predetermined level. Again, this is not essential and a square wave variation of luminance in the transverse direction is possible.

Also, while the invention has been particularly discussed so far in relation to contrast sensitivity function determination, it was indicated initially that this is not an exclusive application. In fact, the particular form of apparatus described above can be operationally modified to suit other applications. For example, the grating can be of uniform spacial frequency, with the subject being required to fixate on a central part of the target and so provide, by control means adjustment, an indication of contrast senstivity in the peripheral visual field. In another variation, the grating can be progressively rotated to provide an indication of directional astigmatism. In yet another variation only one set of bars is of progressively varying luminance and/or dimensions to provide indications of contrast sensitivity relative to different background luminance levels and/or spacial frequencies of different resolution.

Bearing in mind such possibilities for variation, there is provided, in accordance with a general form of the invention, visual faculty testing apparatus comprising: means for presenting a visual target to a subject under test, said target including an array of two sets of areas of respectively different luminance in an alternating sequence in one co-ordinate direction across said array, with the areas of at least one of said sets being of progressively varying luminance towards the luminance of the other of said sets in another co-ordinate direction across said array; and control means adjustable by said subject to alter the rate of said luminance variation.

Apparatus according to the invention will normally comprise an electro-optical screen, suitably in the form of a cathode ray tube, and electronic control means therefor to present the target and effect the desired luminance variations.

Figure 2:
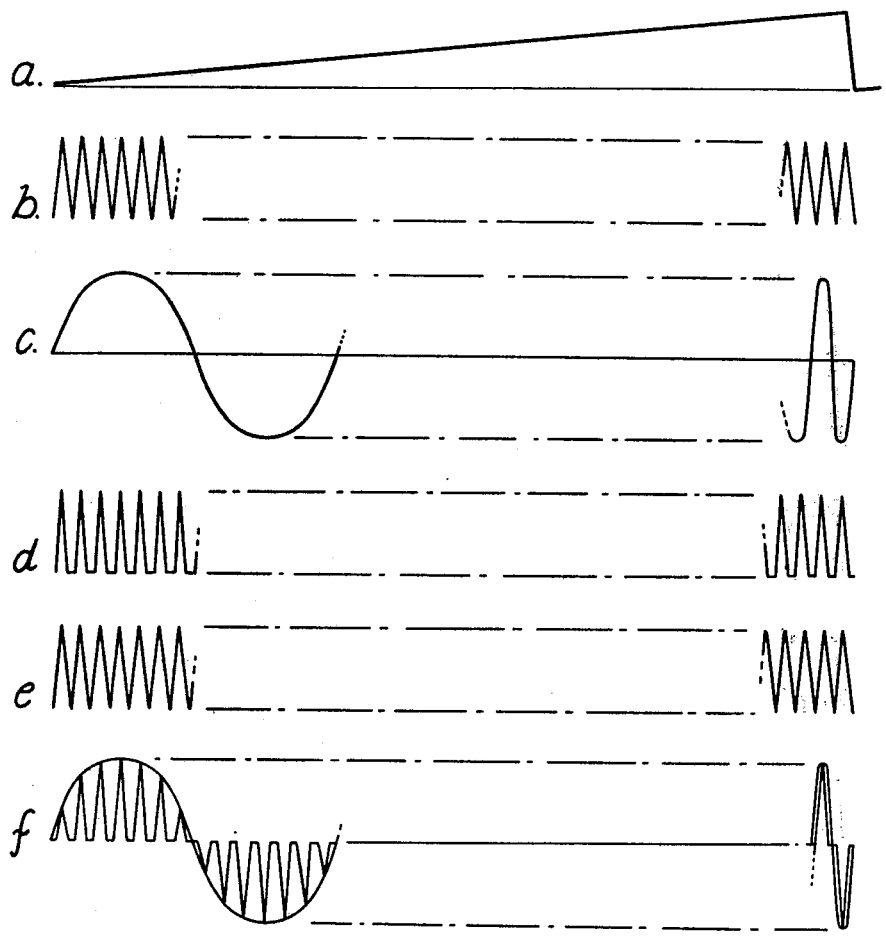
Figure 3:
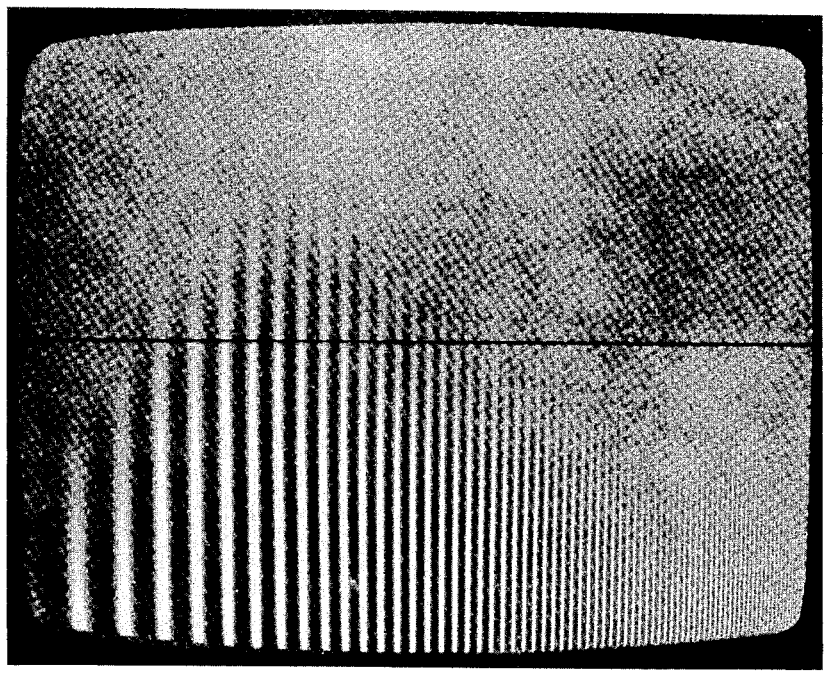
Figure 4:
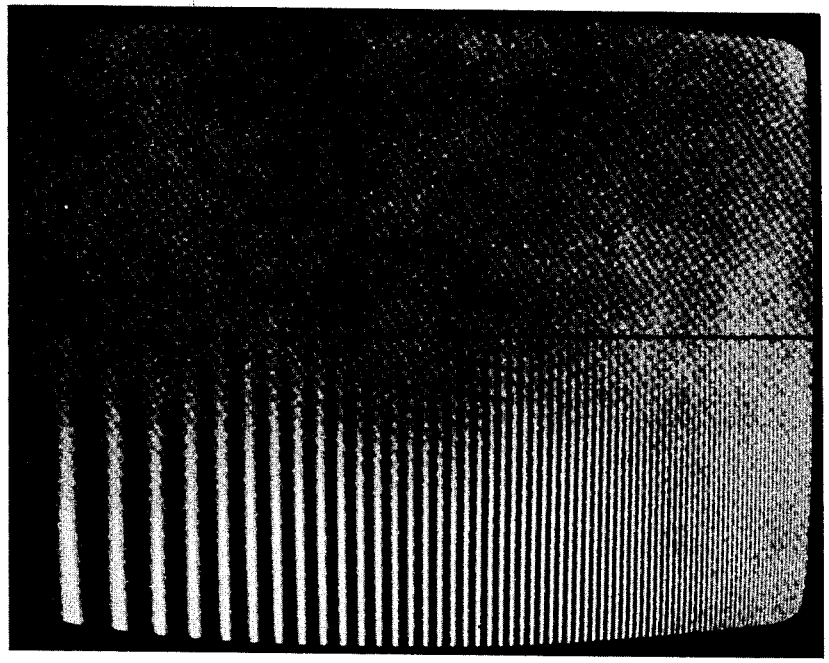

In order that the invention may be more clearly understood, one embodiment of the above-mentioned particular form thereof will now be described, by way of example, with reference to the accompanying drawings, in which:

FIG. 1 schematically illustrates the embodiment;

FIG. 2 illustrates signal waveforms arising during operation of the embodiment;

FIG. 3 diagrammatically illustrates the form of target presented by the embodiment; and FIG. 4 similarly illustrates the target when adjusted to a predetermined pattern.

The illustrated apparatus of FIG. 1 comprises a cathode ray tube 10 operable under the control of a sawtooth time base generator 11 providing an X-input as shown by FIG. 2(a), and a triangle wave oscillator 12 providing a Y-input as shown by FIG. 2(b). The generator 11 and the oscillator 12 operate at frequencies in a similar relationship to those of the frame repetition rate and video modulation frequency in a television system, and are suitably 60 Hz and 150 KHz, respectively.

A Z-input for the tube 10 is provided by a 4-quadrant multiplier 13 which itself has one input from the generator 11 via a swept frequency oscillator 14, and another input from the oscillator 12 via a triangle clipping circuit 15. The output of the swept oscillator 14 is preferably sinusoidal and is shown by FIG. 2(c). The output of the clipping circuit 15 is of constant amplitude, the clipping being effected in respect of the triangle base width and being continuously adjustable between a complete triangle period and a half period as shown by FIGS. 2(d) and 2(e), respectively. The output of the multiplier 13 is shown at FIG. 2(f) for the situation in which the clipper circuit is uniformly adjusted for the whole period of each saw-tooth output from the generator 11 to clip the triangle wave to an extent partway between the clipper limits.

The remaining part of the illustrated apparatus comprises subject controls 16 which include a plurality of subject-adjustable components 17 such as potentiometers connected between the generator 11 and the clipping circuit 15. The components 17 are each operable to vary the degree of clipping effected by the circuit 15 and are respectively associated with successive portions of the sawtooth cycle of generator 11.

Operation of the apparatus with the components 17 set to uniformly adjust the clipping circuit 15 provides a visual output on the tube 10 which will be seen as in FIG. 3 by a subject. The visual output, that is to say, the target, is in the general form of a rectangular grid of parallel bars extending in the Y-direction, the bars being alternately light and dark, and also of increasing spacial frequency in the X-direction. The two sets of respectively light and dark bars are in fact of triangular form, the different luminances are equally and oppositely progressively varied in the Y-direction towards a predetermined level represented by the datum signal level in FIG. 2(f), and the different luminances of the bars vary sinusoidally towards this level in the X-direction from peak luminance levels at their centres. Also, the spacial frequency of the bars progressively varies in the X-direction.

If the components 17 are all set similarly, the Z-input will be of the form shown in FIG. 2(f) and the bars of the target will have different luminance which, from an absolute point of view, extend equally in the Y-direction. However, contrast sensitivity varies with spacial frequency, by decreasing with both increase and decrease of frequency relative to an intermediate value, and so the bars will appear subjectively to extend to varying lengths as shown in FIG. 3.

In use of the embodiment a subject can be asked to adjust the component 17 so that the bars appear to be of equal length as shown in FIG. 4, and the necessary adjustments for this purpose relative to prescribed settings will accordingly represent a contrast sensitivity function characteristic for the subject. Indeed, the adjustments are readily arranged to provide electrical signals which can be suitably recorded to represent the relevant characteristic.

In practice, the spacial frequency of the bars should vary from 0.5 to 30 cycles per degree subtended at the subject's eye.

While the apparatus of the above described embodiment has only been illustrated schematically, thus is considered to be adequate insofar as the relevant waveforms and functions can be obtained with established circuits and techniques, and considerable variation in detail is possible in this respect. For example, the oscillator 12 may have a variable phase output or not, and it need not necessarily provide a symmetrical triangular output. Regarding more general variations within the invention as discussed above: it is evident that variation of spectral frequency can be dispensed with by omission of the swept oscillator 14, that target rotation can be effected by co-ordinate transformation of the cathode ray tube inputs, and so on. Such variations can, of course, be incorporated as selectable options within an apparatus adapted for operation in a number of different operational modes.

We claim:

1. Visual faculty testing apparatus comprising: means for presenting a visual target to a subject under test, said target including an array of two sets of areas of respectively different luminance in an alternating sequence in one co-ordinate direction across said array, with the areas of at least one of said sets being of progressively varying luminance towards the luminance of the other of said sets in another co-ordinate direction across said array; and control means adjustable by said subject to alter the rate of said luminance variation.

2. A visual faculty testing apparatus comprising: means for presenting a visual target to a subject under test, said target being of overall luminance of a predetermined level, said target including an array of two sets of areas of respectively different luminance, said areas of said two sets being in an alternating sequence of progressively varying dimensions in one co-ordinate direction across said array, and said areas of said two sets being of progressively varying luminance in respectively equal and opposite manner towards said predetermined level in another co-ordinate direction across said array; and a plurality of control means respectively operably associated with different zones of said target successively located across said array in said one direction, and control means being selectively adjustably by said subject to alter the respective rates of luminance variation for said zones along said other direction.

3. Apparatus according to claim 2 wherein said array is in the general form of a rectangular grating composed of parallel bars with said one and other co-ordinate directions respectively extending perpendicularly and parallel to the longitudinal direction of said bars.

4. Apparatus according to claim 2 wherein the luminance of each adjacent pair of said areas, one from each of said sets, varies smoothly therebetween in said one direction.

5. Apparatus according to claim 3 wherein the luminance of each adjacent pair of said bars, one from each of said sets, varies sinusoidally therebetween in said one direction.

6. Apparatus according to claim 1 comprising an electro-optical screen and electronic control means therefor to present said target and to selectively adjust the same.

7. Apparatus according to claim 6 wherein said screen is provided by a cathode ray tube.

8. Apparatus according to claim 2 comprising a cathode ray tube and electronic control means therefor to present said target and to selectively adjust the same, said electronic control means including: a sawtooth time base signal generator connected to said cathode ray tube to control the X-scan thereof; a triangular wave oscillator connected to said tube to control the Y-scan thereof; a 4-gradient muliplier connected by way of a swept frequency oscillator for response to said sawtooth generator, connected by way of a constant amplitude clipping circuit for response to said triangular wave oscillator, and connected to said tube to control the Z-input thereof; and a plurality of subject-operable controls connected between said sawtooth generator for respective response to successive portions of each cycle of said generator to determine the degree of clipping effected by said circuit.

* * * * *